(12) United States Patent
Li

(10) Patent No.: US 8,120,783 B2
(45) Date of Patent: Feb. 21, 2012

(54) BIOSENSING APPARATUS AND METHOD USING OPTICAL INTERFERENCE

(76) Inventor: Chian Chiu Li, San Jose, CA (US)

( * ) Notice: Subject to any disclaimer, the term of this patent is extended or adjusted under 35 U.S.C. 154(b) by 499 days.

(21) Appl. No.: 12/365,139

(22) Filed: Feb. 3, 2009

(65) Prior Publication Data

US 2009/0195789 A1    Aug. 6, 2009

Related U.S. Application Data

(60) Provisional application No. 61/025,816, filed on Feb. 4, 2008.

(51) Int. Cl.
    *G01B 9/02*    (2006.01)
    *G01B 11/02*    (2006.01)

(52) U.S. Cl. ..................... 356/521; 356/512

(58) Field of Classification Search .......... 356/454, 356/488, 494, 499, 521, 73, 512; 250/237 G
    See application file for complete search history.

(56) References Cited

U.S. PATENT DOCUMENTS

| 7,768,654 | B2 * | 8/2010 | Cui et al. ............... 356/521 |
| 2008/0024763 | A1 * | 1/2008 | Li ............................ 356/73 |

* cited by examiner

*Primary Examiner* — Patrick J Connolly

(57) ABSTRACT

A label-free interferometric biosensor is disclosed which is based on the self-mixing optical interferometer. Inside the biosensor, an incoming beam is divided into two beam portions which pass through a channel and bio materials, respectively. Interference of the portions is realized by the self-mixing effect and used to detect existence of an analyte, such as DNA or protein molecules. The label-free biosensor is compact and can be made on a chip using the semiconductor technology. It is also convenient to use due to moderate alignment requirement. Furthermore, an array of the interferometers fabricated on a chip enables high-throughput and highly parallel measurements.

20 Claims, 3 Drawing Sheets

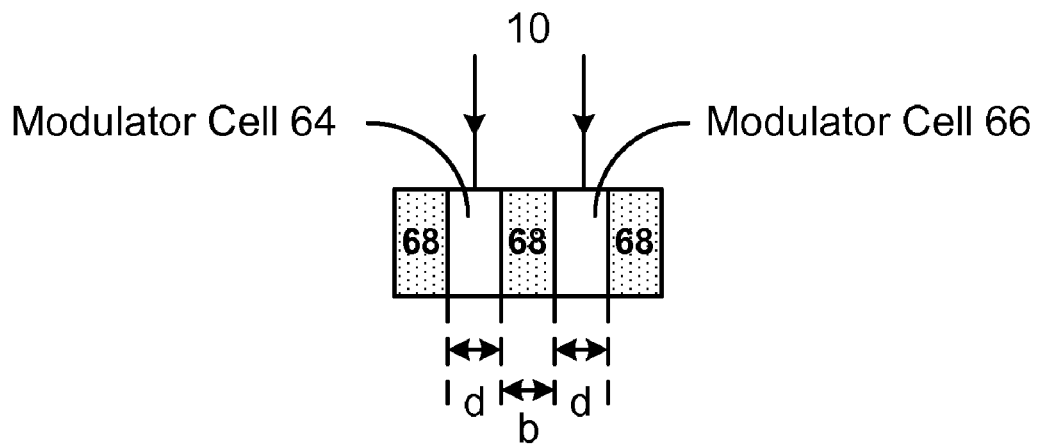
FIG. 1-A (Prior Art)
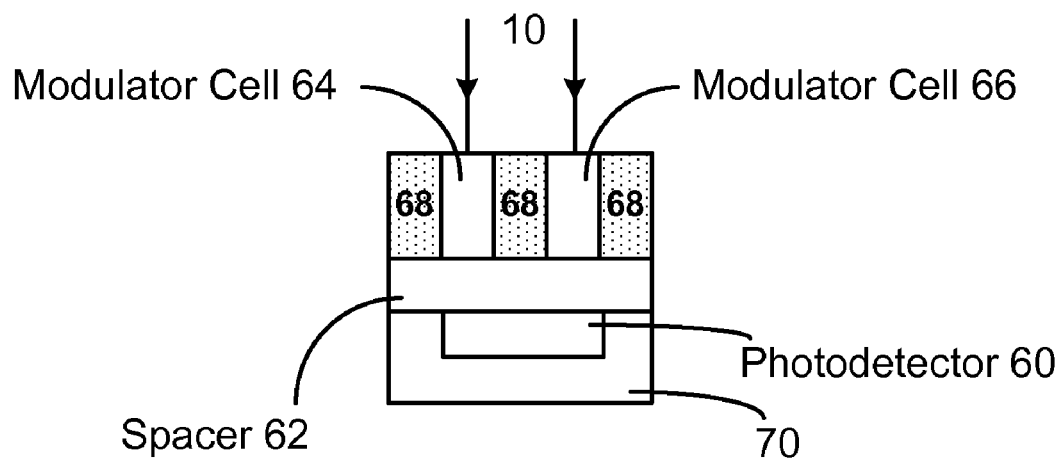
FIG. 1-B (Prior Art)
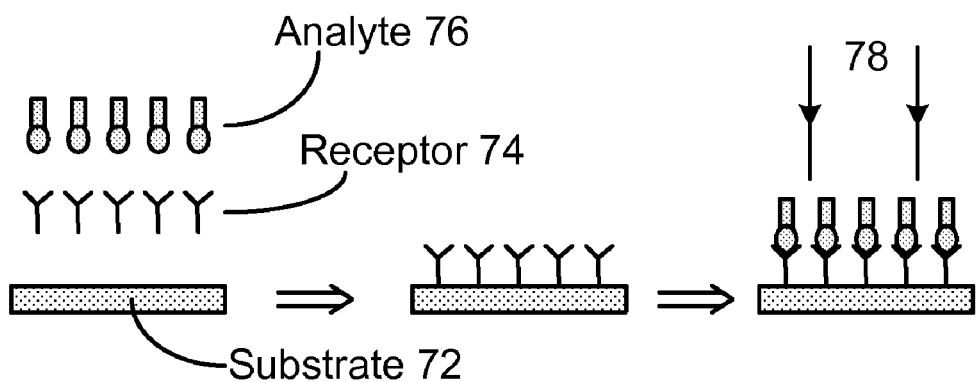
FIG. 1-C (Prior Art)

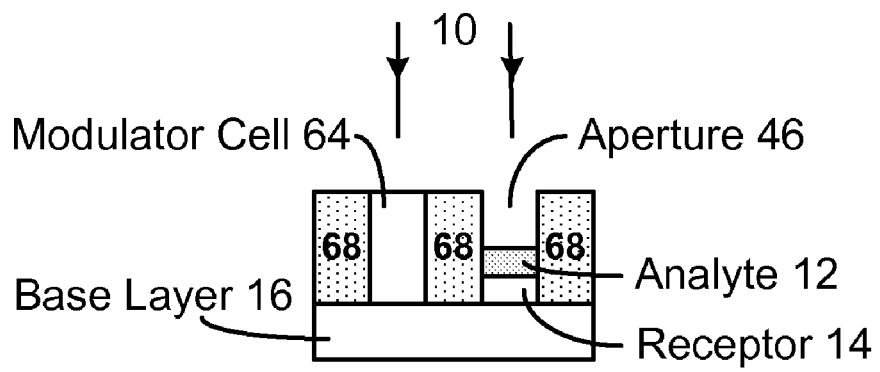
FIG. 2-A
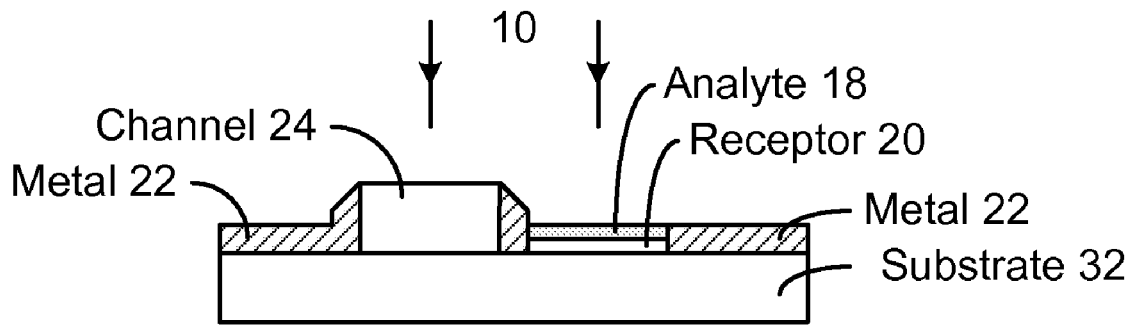
FIG. 2-B
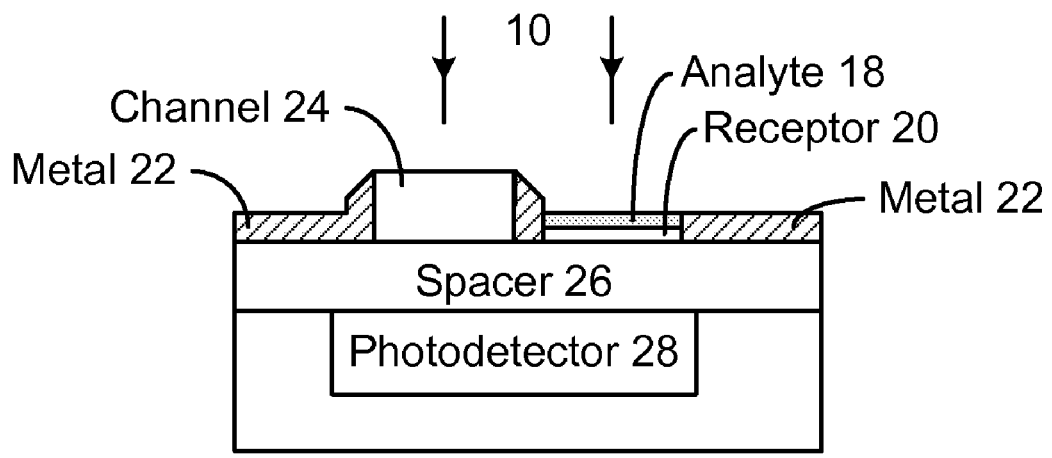
FIG. 2-C

BIOSENSING APPARATUS AND METHOD USING OPTICAL INTERFERENCE

CROSS REFERENCE TO RELATED APPLICATION

This application is entitled to the benefit of Provisional Patent Application Ser. No. 61/025,816, filed Feb. 4, 2008. This application is also related to U.S. application Ser. No. 11/768,265, filed Jun. 26, 2007 now U.S. Pat. No. 8,004,692, and entitled "Optical Interferometer And Method."

FEDERALLY SPONSORED RESEARCH

Not applicable

SEQUENCE LISTING OR PROGRAM

Not applicable

BACKGROUND

1. Field of Invention

This invention relates to biosensors, and particularly to biosensors utilizing optical interference.

2. Description of Prior Art

Deoxyribonucleic acid (DNA) and protein identification are often required in biomedical and healthcare industry. They also play an important role in drug development and homeland security. Currently fluorescent detection is the most used DNA and protein testing method. The fluorescent detection, however, relies on fluorescent labels or tags and suffers from photobleaching, label or tag availability, and limited multiplexing capability. On the other hand, BioCD is a label-free scheme aimed for protein interrogation. But this method needs a compact disc (CD) system in operation. In consequence, the device is bulky in size and inconvenient to use. Device compactness and ease of operation are critical for the much desired on-chip biosensing solutions, such as the emerging lab-on-a-chip (LOC) or micro total analysis system (μTAS).

Therefore, there exists a need for a label-free or tag-free biosensing device which is compact in size and convenient to operate.

OBJECTS AND ADVANTAGES

Accordingly, several main objects and advantages of the present invention are:

a). to provide an improved biosensor;
b). to provide such a biosensor which relies on a label-free test method; and
c). to provide such a biosensor which has a compact structure and is easy to use.

Further objects and advantages will become apparent from a consideration of the drawings and ensuing description.

SUMMARY

In accordance with the present invention, a self-mixing optical interferometer is employed to build a biosensor for test of DNA, protein and other bio samples. The biosensor works by detecting a tiny light path change due to existence of target analyte using the self-mixing interference method. The scheme is label-free and highly sensitive. In addition, because the interferometer is ultra-compact, the biosensor, even having an array of the interferometers, is compact in size. Furthermore, unlike the BioCD with a CD system, it has no moving part and needs only moderate alignment and thus is easy and convenient to use.

ABBREVIATIONS

| | |
|---|---|
| AR | Anti-reflection |
| CD | Compact disc |
| DNA | Deoxyribonucleic acid |
| LOC | Lab-on-a-chip |
| MEMS | Micro-electro-mechanical systems |
| PD | Photodetector |
| μTAS | Micro total analysis system |

DRAWING FIGURES

FIGS. 1-A to 1-C show respectively a prior-art self-mixing optical interferometer, self-mixing interferometer having integrated photodetector (PD), and molecular binding process and test method.

FIGS. 2-A to 2-C are schematic cross-sectional views showing embodiments of biosensors utilizing a self-mixing interferometer according to the invention.

REFERENCE NUMERALS IN DRAWINGS

Figure 3:
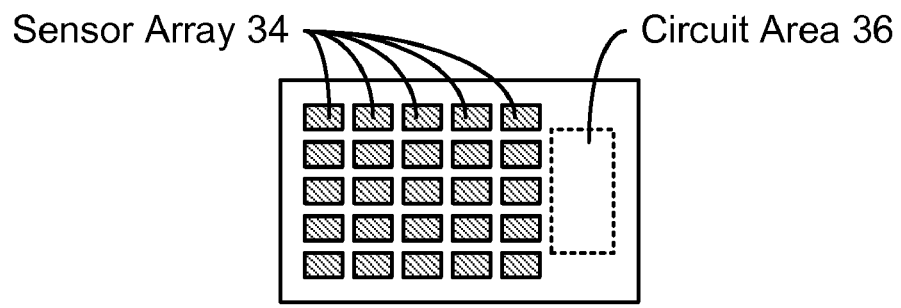
FIG. 3 is a schematic diagram of a biosensing system containing a sensor array and data processing circuitry according to the invention.

| | | | |
|---|---|---|---|
| 10 | Optical beam | 12 | Analyte |
| 14 | Receptor | 16 | Base layer |
| 18 | Analyte | 20 | Receptor |
| 22 | Metal | 24 | Channel |
| 26 | Spacer | 28 | PD |
| 30 | Aperture | 32 | Substrate |
| 34 | Sensor array | 36 | Circuit area |
| 38 | Spacer | 40 | PD |
| 42 | PD | 44 | PD |
| 46 | Aperture | 48 | Channel |
| 60 | PD | 62 | Spacer |
| 64 | Modulator cell | 66 | Modulator cell |
| 68 | Isolation | 70 | Substrate |
| 72 | Substrate | 74 | Receptor |
| 76 | Analyte | 78 | Optical beam |

DETAILED DESCRIPTION

FIGS. 1-A to 1-C—Prior-Art

FIG. 1-A shows a cross-sectional view of a prior-art self-mixing optical interferometer. An incident beam 10 is transmitted to impinge on a spatial phase modulator and passes through modulator cells 64 and 66 respectively. Around the modulator cells are isolation regions 68 which block light transmission. The modulator cells have a dimension d and are spaced apart by a distance b along a direction perpendicular to the beam propagation. Values of d and b are chosen small enough, for example, around or smaller than the wavelength of the beam. Due to diffraction, beam expansion happens after the beams pass through and come out of the modulator cells. Beam spreading and small beam spacing together cause the self-mixing effect and interference happens between the beams. As a result, a focus lens, which is required for a conventional free-space interferometer, is no longer needed for mixing the beams and the interferometer can be made ultra-compact.

Another prior-art self-mixing interferometer is shown in FIG. 1-B in a cross-sectional view. It contains an integrated PD 60. The interferometer structure is similar to the one of FIG. 1-A. PD 60, which receives optical signals and converts them to electrical currents, is fabricated on a substrate 70. A layer 62 works as a spacer region. When beams emerge from modulator cells 64 and 66, they spread and self-mix in the spacer region before entering PD 60. The schemes in FIGS. 1-A and 1-B provide a simple and compact structure for a modulator or interferometer, which also enables fabrication using the semiconductor technology. Dimensions of b and d can be as small as sub-micrometer or even in the nanoscale range, i.e. smaller than 100 nm.

Shown in FIG. 1-C is a prior-art molecular binding process and detection method, where a receptor 74 is adsorbed on a substrate 72 first and then the receptor binds a molecular analyte 76. Typically, a receptor is chosen such that it binds only one particular analyte which includes cells, viruses, bacteria, toxins, peptides, DNA fragments, antibodies, venoms, oligo-saccharides, proteins, etc. Without the analyte, a probe beam 78 only experiences phase delay caused by the receptor and substrate. But when an analyte is introduced and bound by the receptor, the beam undergoes additional phase delay due to the analyte. Thus the value of phase delay of the probe beam can be used to detect the presence of an analyte. Since the method does not involve fluorescent labels, it is of label-free detection.

FIGS. 2-A to 2-C Embodiments Of Biosensors Using Interference

FIG. 2-A depicts schematically a cross-sectional view of a biosensor embodiment, which utilizes the self-mixing optical interference and employs the structure shown in FIG. 1-A. Beam 10 is split into two portions by wavefront division, one going through modulator cell 64 while the other through an aperture 46. Interference of the two portions is used for biosensing. The test procedures are as follows. A receptor 14 which may be a receptor layer is pre-adsorbed on a base layer 16 in the aperture. After causing a target analyte 12 to interact with the receptor in a liquid or gaseous environment, the analyte is bound to the receptor. Next beam 10 is turned on to produce two beam portions and then the self-mixing interference.

Without the binding between the analyte and receptor, a beam portion, going through the aperture, passes receptor 14 and base layer 16 only, which results in certain interference intensity. Once the binding occurs, the portion has to pass the analyte besides the receptor and base layer. The analyte generates additional phase delay and changes the interference intensity. Since the analyte, if viewed as a layer, is very thin and affects the phase delay only slightly, a highly sensitive test is needed, which makes an interferometric detection a desired choice.

The self-mixing interference can be tuned by the dimension and material of cell 64 and aperture 46. In order to have a sensitive measurement, for example, the phase difference between the portions can be arranged to be around one half of pi where the interference intensity changes not only most but also most linearly versus change of the phase difference. Because a liquid or gas may contain bio materials that influence phase retardation, it is preferred to take a test when the analyte is exposed in the air.

The device structure of FIG. 2-A may be modified a bit as shown schematically in FIG. 2-B, where a substrate 32 may be a glass or a sheet made by silicon dioxide deposition, a channel 24 may be made up of silicon dioxide, a metal layer 22 may be of chromium, aluminum, or gold and functions as a light blocker and beam portion divider. Again, a receptor 20 is pre-adsorbed on substrate 32. After a sample solution is brought in to interact with the receptor, beam 10 is used to detect presence of an analyte 18 by optical interference. The structure can be readily fabricated by mature semiconductor technology.

The biosensor structure of FIG. 2-B can be integrated with a PD. FIG. 2-C shows a schematic cross-sectional view of such a device, which basically replaces substrate 32 with a spacer 26 and builds the structure of FIG. 2-B atop a PD 28. The resulting device is more compact and because a photodiode-type PD can be fabricated using the same process as integrated circuits, multiple functions can be integrated to form a sensing system on a chip, as shown in the following.

The biosensor of FIG. 2-C forms a stand-alone biosensing system. It uses a label-free optical interferometric method. It is of on-chip type and has an ultra-compact structure. Furthermore, unlike other optical systems where accurate alignment is required in order to avoid severe loss of optical signals, the embodiment needs only moderate alignment, especially in the case in which a thick beam is used. Thus the biosensor is label free, compact, and easy to operate.

Figure 4:
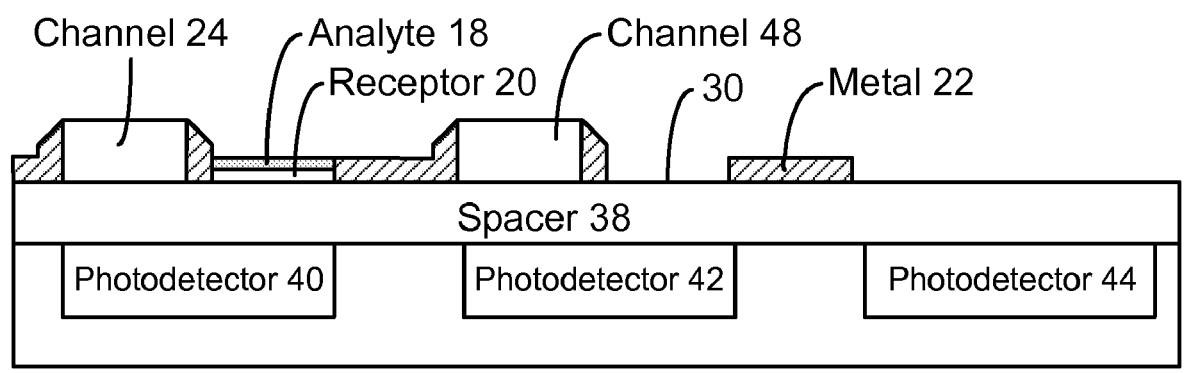
FIG. 4 is a cross-sectional view showing schematically a biosensor embodiment where multiple interferometers as well as power monitor are employed.

FIGS. 3 and 4 Embodiments of Biosensors Using Interference

Aforementioned devices can be used to create on-chip biosensing systems like LOC or µTAS. One example is shown graphically in FIG. 3, where a sensor array 34 is built for parallel tests, which enables high-multiplexing and high-throughput detection. In the figure, each cell of the array may have the structure as described in FIG. 2-C and a circuit area 36 may comprise integrated circuits of amplifiers, signal readout control, and processors. It is noted that microfluidic components, such as micron or sub-micron sized channels, electrophoresis functions, micro-valves, micro-pumps, micro-switches, and other micro-electro-mechanical-systems (MEMS) based structures may also be incorporated in the system of FIG. 3. The microfluidic features are not shown for simplicity purpose as they are well known in the field.

In order to implement differential method for high-resolution measurements, a pair of data is needed for each test. For such a purpose, FIG. 4 shows schematically a cross-sectional view of a device having two interferometers. One interferometer is similar to the one of FIG. 2-C, comprising channel 24, PD 40, receptor 20, and possibly, analyte 18. The other interferometer contains a channel 48, a PD 42, and an aperture 30 through which one beam portion passes. Spacer 38 serves as a beam mixing region for the interferometers. A PD 44 or multiple units of such PD may also be arranged nearby for calibration and monitoring of the incident optical power around the interferometers. During operation, PDs 40 and 42 receive signals of interference intensities respectively and produce different electrical currents, which are designed for differential data processing and used to detect an analyte with high resolution.

CONCLUSION, RAMIFICATIONS, AND SCOPE

Thus it can be seen that the self-mixing optical interferometer is utilized to provide an improved biosensor.

The biosensor has the following advantages: Label-free detection, compactness, and ease of use.

Although the description above contains many specificities, these should not be construed as limiting the scope of the invention but as merely providing illustrations of some of the presently preferred embodiments. Numerous modifications will be obvious to those skilled in the art.

Ramifications:

Anti-reflection (AR) coating may be deposited to the exposed surfaces where a beam passes through to reduce power loss and signal noise. AR coating may also be added to interface between two layers of different indexes of refraction for the same purpose.

The modulator cells mentioned in the above may be made tunable. For example, liquid crystal, Lithium Niobate, and other electro-opto materials may be used whose refractive indexes can be tuned by electrical means.

Lastly, all interferometers or sensor units introduced in the above can have dimensions in nanoscale range in the direction perpendicular to the light propagation.

Therefore the scope of the invention should be determined by the appended claims and their legal equivalents, rather than by the examples given.

The invention claimed is:

1. An optical apparatus comprising:
   1) a plurality of spatial phase modulators, said modulators being arranged to divide an optical beam into at least a plurality of first beam portions and a plurality of second beam portions by wavefront division and to produce phase shift on said first and second beam portions respectively;
   2) bio means for arranging a biological, biomedical, or biochemical medium, said medium arranged such that the phase of one of said first or second beam portions is also influenced by said medium;
   3) isolation means for reducing crosstalk between one of said first and one of said second beam portions;
   4) interference means for producing optical interference among said first beam portions and among said second beam portions respectively;
   5) a plurality of detectors for detecting a plurality of signals of said interference respectively; and
   6) data means for performing differential operation using said plurality of signals.

2. The apparatus according to claim 1, further including tuning means for tuning the phase of one of said first or second beam portions.

3. The apparatus according to claim 1, further including microfluidic means for handling a sample under test using micro fluidics.

4. The apparatus according to claim 1 wherein at least one of said first beam portions is arranged such that its beam width along a direction perpendicular to its propagation is around or smaller than the wavelength of said beam.

5. The apparatus according to claim 1 wherein said modulators and said detectors are arranged to be disposed on one substrate.

6. The apparatus according to claim 1, further including power monitoring means for monitoring the power of said beam.

7. An optical apparatus comprising:
   1) a plurality of spatial phase modulators, said modulators being arranged to divide an optical beam into at least a plurality of first beam portions and a plurality of second beam portions by wavefront division and to produce phase shift on said first and second beam portions respectively;
   2) bio means for arranging a biological, biomedical, or biochemical medium, said medium arranged such that the phase of one of said first or second beam portions is also influenced by said medium;
   3) isolation means for reducing crosstalk between one of said first and one of said second beam portions;
   4) interference means for producing optical interference among said first beam portions and among said second beam portions respectively;
   5) a plurality of first detectors for detecting a plurality of signals of said interference respectively; and
   6) at least a second detector for monitoring the power of said beam, said second detector arranged in substantial proximity to at least one of said modulators or one of said first detectors.

8. The apparatus according to claim 7, further including microfluidic means for handling a sample under test using micro fluidics.

9. The apparatus according to claim 7 wherein at least two of said first beam portions are disposed such that they are spaced apart by a distance around or smaller than the wavelength of said beam.

10. The apparatus according to claim 7 wherein at least one of said first beam portions is arranged such that its beam width along a direction perpendicular to its propagation is around or smaller than the wavelength of said beam.

11. The apparatus according to claim 7 wherein said modulators and said first detectors are arranged to be disposed on one substrate.

12. The apparatus according to claim 7, further including differential means for performing differential measurements using said plurality of signals.

13. The apparatus according to claim 7, further including tuning means for tuning the phase of one of said first or second beam portions.

14. An optical apparatus comprising:
   1) a plurality of spatial phase modulators, said modulators being arranged to divide an optical beam into at least a plurality of first beam portions and a plurality of second beam portions and to produce phase shift on said first and second beam portions respectively;
   2) microfluidic means for handling a sample under test using micro fluidics;
   3) isolation means for reducing crosstalk between one of said first and one of said second beam portions;
   4) interference means for producing optical interference among said first beam portions and among said second beam portions respectively;
   5) a plurality of detectors for detecting a plurality of signals of said interference respectively; and
   6) integration means for arranging said modulators and detectors on a substrate, the normal of said substrate and the propagation direction of said beam arranged to form an angle smaller than eighty degrees for one segment of the propagation above said substrate.

15. The apparatus according to claim 14, further including bio means for arranging a biological, biomedical, or biochemical medium, said medium arranged such that the phase of one of said first or second beam portions is also influenced by said medium.

16. The apparatus according to claim 14 wherein at least two of said first beam portions are disposed such that they are spaced apart by a distance around or smaller than the wavelength of said beam.

17. The apparatus according to claim 14 wherein at least one of said first beam portions is arranged such that its beam width along a direction perpendicular to its propagation is around or smaller than the wavelength of said beam.

18. The apparatus according to claim 14, further including differential means for performing differential measurements using said plurality of signals.

19. The apparatus according to claim 14, further including tuning means for tuning the phase of one of said first or second beam portions.

20. The apparatus according to claim 14, further including power monitoring means for monitoring the power of said beam.

* * * * *